United States Patent [19]
Toft et al.

[11] Patent Number: 5,928,381
[45] Date of Patent: Jul. 27, 1999

[54] USE OF AN α-AMYLASE MODIFIED TO IMPROVE OXIDATION STABILITY IN A COMBINED DESIZING AND BLEACHING PROCESS

[75] Inventors: Annette Hanne Toft, Bagsværd; Dorthe Marcher, Farum; Hanne Høst Pedersen, Lyngby; Thomas Erik Nilsson, Copenhagen Ø, all of Denmark

[73] Assignee: Novo Nordisk A/S, Bagsvaerd, Denmark

[21] Appl. No.: 08/687,399

[22] PCT Filed: Oct. 5, 1994

[86] PCT No.: PCT/DK94/00371

§ 371 Date: Aug. 22, 1996

§ 102(e) Date: Aug. 22, 1996

[87] PCT Pub. No.: WO95/21247

PCT Pub. Date: Aug. 10, 1995

[30] Foreign Application Priority Data

Feb. 2, 1994 [DK] Denmark .................. 0141/94

[51] Int. Cl.⁶ .............. C12N 9/28; C12N 15/56; D06L 1/14; C11D 3/386
[52] U.S. Cl. ............ 8/111; 8/101; 8/107; 8/138; 510/305; 510/392; 510/393; 435/263
[58] Field of Search ............ 8/101, 107, 111, 8/138; 510/305, 392, 393; 435/263

[56] References Cited

U.S. PATENT DOCUMENTS 4,536,182   8/1985   Tatin ........................... 8/138

FOREIGN PATENT DOCUMENTS

WO91/00353   1/1991   WIPO.
WO91/16423   10/1991  WIPO.
WO 94/02597  2/1994   WIPO.
WO 94/18314  8/1994   WIPO.

OTHER PUBLICATIONS

Esteil et al, "Engineering an Enzyme by Site–Directed Mutagenesis to be Resistant to Chemical Oxidation", J. Biol. Chem, 260(11), Jun., 1985, pp. 6518–6521.

*Primary Examiner*—Alan Diamond
*Attorney, Agent, or Firm*—Steve T. Zelson, Esq.; Valeta A. Gregg, Esq.

[57] ABSTRACT

A process for simultaneously desizing and bleaching of a sized fabric containing starch or starch derivatives, which process comprises treating the fabric with a bleaching composition and an oxidation stable α-amylase.

16 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
　　　　(A) LENGTH: 1920 base pairs
　　　　(B) TYPE: nucleic acid
　　　　(C) STRANDEDNESS: single
　　　　(D) TOPOLOGY: linear (ii) MOLECULE TYPE: DNA (genomic)

(ix) FEATURE:
　　　　(A) NAME/KEY: CDS
　　　　(B) LOCATION: 334..1869

(ix) FEATURE:
　　　　(A) NAME/KEY: sig_peptide
　　　　(B) LOCATION: 334..420

(ix) FEATURE:

(A) NAME/KEY: mat_peptide
(B) LOCATION: 421..1869

(xi) SEQUENCE DESCRIPTION: SEQ ID NO:1:

```
CGGAAGATTG GAAGTACAAA AATAAGCAAA AGATTGTCAA TCATGTCATG AGCCATGCGG         60

GAGACGGAAA AATCGTCTTA ATGCACGATA TTTATGCAAC GTTCGCAGAT GCTGCTGAAG        120

AGATTATTAA AAAGCTGAAA GCAAAAGGCT ATCAATTGGT AACTGTATCT CAGCTTGAAG        180

AAGTGAAGAA GCAGAGAGGC TATTGAATAA ATGAGTAGAA GCGCCATATC GGCGCTTTTC        240

TTTTGGAAGA AATATAGGG AAAATGGTAC TTGTTAAAAA TTCGGAATAT TTATACAACA         300

TCATATGTTT CACATTGAAA GGGGAGGAGA ATC ATG AAA CAA CAA AAA CGG CTT        354
                                    Met Lys Gln Gln Lys Arg Leu
                                    -29             -25

TAC GCC CGA TTG CTG ACG CTG TTA TTT GCG CTC ATC TTC TTG CTG CCT         402
Tyr Ala Arg Leu Leu Thr Leu Leu Phe Ala Leu Ile Phe Leu Leu Pro
        -20              -15              -10

CAT TCT GCA GCA GCG GCG GCA AAT CTT AAT GGG ACG CTG ATG CAG TAT         450
His Ser Ala Ala Ala Ala Ala Asn Leu Asn Gly Thr Leu Met Gln Tyr
    -5                        1               5              10

TTT GAA TGG TAC ATG CCC AAT GAC GGC CAA CAT TGG AGG CGT TTG CAA         498
Phe Glu Trp Tyr Met Pro Asn Asp Gly Gln His Trp Arg Arg Leu Gln
             15              20              25

AAC GAC TCG GCA TAT TTG GCT GAA CAC GGT ATT ACT GCC GTC TGG ATT         546
Asn Asp Ser Ala Tyr Leu Ala Glu His Gly Ile Thr Ala Val Trp Ile
        30              35              40

CCC CCG GCA TAT AAG GGA ACG AGC CAA GCG GAT GTG GGC TAC GGT GCT         594
Pro Pro Ala Tyr Lys Gly Thr Ser Gln Ala Asp Val Gly Tyr Gly Ala
        45              50              55

TAC GAC CTT TAT GAT TTA GGG GAG TTT CAT CAA AAA GGG ACG GTT CGG         642
Tyr Asp Leu Tyr Asp Leu Gly Glu Phe His Gln Lys Gly Thr Val Arg
    60              65              70

ACA AAG TAC GGC ACA AAA GGA GAG CTG CAA TCT GCG ATC AAA AGT CTT         690
Thr Lys Tyr Gly Thr Lys Gly Glu Leu Gln Ser Ala Ile Lys Ser Leu
75              80              85              90

CAT TCC CGC GAC ATT AAC GTT TAC GGG GAT GTG GTC ATC AAC CAC AAA         738
His Ser Arg Asp Ile Asn Val Tyr Gly Asp Val Val Ile Asn His Lys
             95              100             105

GGC GGC GCT GAT GCG ACC GAA GAT GTA ACC GCG GTT GAA GTC GAT CCC         786
Gly Gly Ala Asp Ala Thr Glu Asp Val Thr Ala Val Glu Val Asp Pro
        110             115             120

GCT GAC CGC AAC CGC GTA ATT TCA GGA GAA CAC CTA ATT AAA GCC TGG         834
Ala Asp Arg Asn Arg Val Ile Ser Gly Glu His Leu Ile Lys Ala Trp
        125             130             135

ACA CAT TTT CAT TTT CCG GGG CGC GGC AGC ACA TAC AGC GAT TTT AAA         882
Thr His Phe His Phe Pro Gly Arg Gly Ser Thr Tyr Ser Asp Phe Lys
    140             145             150

TGG CAT TGG TAC CAT TTT GAC GGA ACC GAT TGG GAC GAG TCC CGA AAG         930
Trp His Trp Tyr His Phe Asp Gly Thr Asp Trp Asp Glu Ser Arg Lys
155             160             165             170

CTG AAC CGC ATC TAT AAG TTT CAA GGA AAG GCT TGG GAT TGG GAA GTT         978
Leu Asn Arg Ile Tyr Lys Phe Gln Gly Lys Ala Trp Asp Trp Glu Val
             175             180             185

TCC AAT GAA AAC GGC AAC TAT GAT TAT TTG ATG TAT GCC GAC ATC GAT        1026
Ser Asn Glu Asn Gly Asn Tyr Asp Tyr Leu Met Tyr Ala Asp Ile Asp
        190             195             200

TAT GAC CAT CCT GAT GTC GCA GCA GAA ATT AAG AGA TGG GGC ACT TGG        1074
Tyr Asp His Pro Asp Val Ala Ala Glu Ile Lys Arg Trp Gly Thr Trp
        205             210             215

TAT GCC AAT GAA CTG CAA TTG GAC GGT TTC CGT CTT GAT GCT GTC AAA        1122
```

```
Tyr Ala Asn Glu Leu Gln Leu Asp Gly Phe Arg Leu Asp Ala Val Lys
220                 225                 230

CAC ATT AAA TTT TCT TTT TTG CGG GAT TGG GTT AAT CAT GTC AGG GAA    1170
His Ile Lys Phe Ser Phe Leu Arg Asp Trp Val Asn His Val Arg Glu
235                 240                 245                 250

AAA ACG GGG AAG GAA ATG TTT ACG GTA GCT GAA TAT TGG CAG AAT GAC    1218
Lys Thr Gly Lys Glu Met Phe Thr Val Ala Glu Tyr Trp Gln Asn Asp
            255                 260                 265

TTG GGC GCG CTG GAA AAC TAT TTG AAC AAA ACA AAT TTT AAT CAT TCA    1266
Leu Gly Ala Leu Glu Asn Tyr Leu Asn Lys Thr Asn Phe Asn His Ser
        270                 275                 280

GTG TTT GAC GTG CCG CTT CAT TAT CAG TTC CAT GCT GCA TCG ACA CAG    1314
Val Phe Asp Val Pro Leu His Tyr Gln Phe His Ala Ala Ser Thr Gln
    285                 290                 295

GGA GGC GGC TAT GAT ATG AGG AAA TTG CTG AAC GGT ACG GTC GTT TCC    1362
Gly Gly Gly Tyr Asp Met Arg Lys Leu Leu Asn Gly Thr Val Val Ser
300                 305                 310

AAG CAT CCG TTG AAA TCG GTT ACA TTT GTC GAT AAC CAT GAT ACA CAG    1410
Lys His Pro Leu Lys Ser Val Thr Phe Val Asp Asn His Asp Thr Gln
315                 320                 325                 330

CCG GGG CAA TCG CTT GAG TCG ACT GTC CAA ACA TGG TTT AAG CCG CTT    1458
Pro Gly Gln Ser Leu Glu Ser Thr Val Gln Thr Trp Phe Lys Pro Leu
            335                 340                 345

GCT TAC GCT TTT ATT CTC ACA AGG GAA TCT GGA TAC CCT CAG GTT TTC    1506
Ala Tyr Ala Phe Ile Leu Thr Arg Glu Ser Gly Tyr Pro Gln Val Phe
        350                 355                 360

TAC GGG GAT ATG TAC GGG ACG AAA GGA GAC TCC CAG CGC GAA ATT CCT    1554
Tyr Gly Asp Met Tyr Gly Thr Lys Gly Asp Ser Gln Arg Glu Ile Pro
    365                 370                 375

GCC TTG AAA CAC AAA ATT GAA CCG ATC TTA AAA GCG AGA AAA CAG TAT    1602
Ala Leu Lys His Lys Ile Glu Pro Ile Leu Lys Ala Arg Lys Gln Tyr
380                 385                 390

GCG TAC GGA GCA CAG CAT GAT TAT TTC GAC CAC CAT GAC ATT GTC GGC    1650
Ala Tyr Gly Ala Gln His Asp Tyr Phe Asp His His Asp Ile Val Gly
395                 400                 405                 410

TGG ACA AGG GAA GGC GAC AGC TCG GTT GCA AAT TCA GGT TTG GCG GCA    1698
Trp Thr Arg Glu Gly Asp Ser Ser Val Ala Asn Ser Gly Leu Ala Ala
            415                 420                 425

TTA ATA ACA GAC GGA CCC GGT GGG GCA AAG CGA ATG TAT GTC GGC CGG    1746
Leu Ile Thr Asp Gly Pro Gly Gly Ala Lys Arg Met Tyr Val Gly Arg
        430                 435                 440

CAA AAC GCC GGT GAG ACA TGG CAT GAC ATT ACC GGA AAC CGT TCG GAG    1794
Gln Asn Ala Gly Glu Thr Trp His Asp Ile Thr Gly Asn Arg Ser Glu
    445                 450                 455

CCG GTT GTC ATC AAT TCG GAA GGC TGG GGA GAG TTT CAC GTA AAC GGC    1842
Pro Val Val Ile Asn Ser Glu Gly Trp Gly Glu Phe His Val Asn Gly
460                 465                 470

GGG TCG GTT TCA ATT TAT GTT CAA AGA TAGAAGAGCA GAGAGGACGG          1889
Gly Ser Val Ser Ile Tyr Val Gln Arg
475                 480

ATTTCCTGAA GGAAATCCGT TTTTTTATTT T                                 1920

(2) INFORMATION FOR SEQ ID NO:2:

(i) SEQUENCE CHARACTERISTICS:
        (A) LENGTH: 512 amino acids
        (B) TYPE: amino acid
        (D) TOPOLOGY: linear (ii) MOLECULE TYPE: protein (xi) SEQUENCE DESCRIPTION: SEQ ID NO:2:
```

```
Met Lys Gln Gln Lys Arg Leu Tyr Ala Arg Leu Leu Thr Leu Leu Phe
-29             -25                 -20                 -15

Ala Leu Ile Phe Leu Leu Pro His Ser Ala Ala Ala Ala Asn Leu
            -10                  -5                   1

Asn Gly Thr Leu Met Gln Tyr Phe Glu Trp Tyr Met Pro Asn Asp Gly
         5                  10                  15

Gln His Trp Arg Arg Leu Gln Asn Asp Ser Ala Tyr Leu Ala Glu His
 20                  25                  30                  35

Gly Ile Thr Ala Val Trp Ile Pro Pro Ala Tyr Lys Gly Thr Ser Gln
                 40                  45                  50

Ala Asp Val Gly Tyr Gly Ala Tyr Asp Leu Tyr Asp Leu Gly Glu Phe
                 55                  60                  65

His Gln Lys Gly Thr Val Arg Thr Lys Tyr Gly Thr Lys Gly Glu Leu
             70                  75                  80

Gln Ser Ala Ile Lys Ser Leu His Ser Arg Asp Ile Asn Val Tyr Gly
 85                  90                  95

Asp Val Val Ile Asn His Lys Gly Gly Ala Asp Ala Thr Glu Asp Val
100                 105                 110                 115

Thr Ala Val Glu Val Asp Pro Ala Asp Arg Asn Arg Val Ile Ser Gly
                120                 125                 130

Glu His Leu Ile Lys Ala Trp Thr His Phe His Phe Pro Gly Arg Gly
             135                 140                 145

Ser Thr Tyr Ser Asp Phe Lys Trp His Trp Tyr His Phe Asp Gly Thr
             150                 155                 160

Asp Trp Asp Glu Ser Arg Lys Leu Asn Arg Ile Tyr Lys Phe Gln Gly
165                 170                 175

Lys Ala Trp Asp Trp Glu Val Ser Asn Glu Asn Gly Asn Tyr Asp Tyr
180                 185                 190                 195

Leu Met Tyr Ala Asp Ile Asp Tyr Asp His Pro Asp Val Ala Ala Glu
                200                 205                 210

Ile Lys Arg Trp Gly Thr Trp Tyr Ala Asn Glu Leu Gln Leu Asp Gly
             215                 220                 225

Phe Arg Leu Asp Ala Val Lys His Ile Lys Phe Ser Phe Leu Arg Asp
         230                 235                 240

Trp Val Asn His Val Arg Glu Lys Thr Gly Lys Glu Met Phe Thr Val
         245                 250                 255

Ala Glu Tyr Trp Gln Asn Asp Leu Gly Ala Leu Glu Asn Tyr Leu Asn
260                 265                 270                 275

Lys Thr Asn Phe Asn His Ser Val Phe Asp Val Pro Leu His Tyr Gln
             280                 285                 290

Phe His Ala Ala Ser Thr Gln Gly Gly Gly Tyr Asp Met Arg Lys Leu
             295                 300                 305

Leu Asn Gly Thr Val Val Ser Lys His Pro Leu Lys Ser Val Thr Phe
             310                 315                 320

Val Asp Asn His Asp Thr Gln Pro Gly Gln Ser Leu Glu Ser Thr Val
             325                 330                 335

Gln Thr Trp Phe Lys Pro Leu Ala Tyr Ala Phe Ile Leu Thr Arg Glu
340                 345                 350                 355

Ser Gly Tyr Pro Gln Val Phe Tyr Gly Asp Met Tyr Gly Thr Lys Gly
                360                 365                 370

Asp Ser Gln Arg Glu Ile Pro Ala Leu Lys His Lys Ile Glu Pro Ile
             375                 380                 385

Leu Lys Ala Arg Lys Gln Tyr Ala Tyr Gly Ala Gln His Asp Tyr Phe
```

-continued

```
          390                 395                400
Asp His His Asp Ile Val Gly Trp Thr Arg Glu Gly Asp Ser Ser Val
    405                 410                415

Ala Asn Ser Gly Leu Ala Ala Leu Ile Thr Asp Gly Pro Gly Gly Ala
420                 425                 430                435

Lys Arg Met Tyr Val Gly Arg Gln Asn Ala Gly Glu Thr Trp His Asp
                440                 445                 450

Ile Thr Gly Asn Arg Ser Glu Pro Val Val Ile Asn Ser Glu Gly Trp
                455                 460                 465

Gly Glu Phe His Val Asn Gly Ser Val Ser Ile Tyr Val Gln Arg
                470                 475                 480
```

(2) INFORMATION FOR SEQ ID NO:3:

(i) SEQUENCE CHARACTERISTICS:
        (A) LENGTH: 2084 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: sig_peptide
        (B) LOCATION: 250..342

(ix) FEATURE:
        (A) NAME/KEY: CDS
        (B) LOCATION: 250..1791

(ix) FEATURE:
        (A) NAME/KEY: mat_peptide
        (B) LOCATION: 343..1791

(xi) SEQUENCE DESCRIPTION: SEQ ID NO:3:

```
GCCCCGCACA TACGAAAAGA CTGGCTGAAA ACATTGAGCC TTTGATGACT GATGATTTGG      60

CTGAAGAAGT GGATCGATTG TTTGAGAAAA GAAGAAGACC ATAAAAATAC CTTGTCTGTC     120

ATCAGACAGG GTATTTTTTA TGCTGTCCAG ACTGTCCGCT GTGTAAAAAT AAGGAATAAA     180

GGGGGGTTGT TATTATTTTA CTGATATGTA AAATATAATT TGTATAAGAA AATGAGAGGG     240

AGAGGAAAC ATG ATT CAA AAA CGA AAG CGG ACA GTT TCG TTC AGA CTT          288
          Met Ile Gln Lys Arg Lys Arg Thr Val Ser Phe Arg Leu
          -31 -30             -25                 -20

GTG CTT ATG TGC ACG CTG TTA TTT GTC AGT TTG CCG ATT ACA AAA ACA        336
Val Leu Met Cys Thr Leu Leu Phe Val Ser Leu Pro Ile Thr Lys Thr
            -15             -10                 -5

TCA GCC GTA AAT GGC ACG CTG ATG CAG TAT TTT GAA TGG TAT ACG CCG        384
Ser Ala Val Asn Gly Thr Leu Met Gln Tyr Phe Glu Trp Tyr Thr Pro
    1               5                   10

AAC GAC GGC CAG CAT TGG AAA CGA TTG CAG AAT GAT GCG GAA CAT TTA        432
Asn Asp Gly Gln His Trp Lys Arg Leu Gln Asn Asp Ala Glu His Leu
15              20                  25                  30

TCG GAT ATC GGA ATC ACT GCC GTC TGG ATT CCT CCC GCA TAC AAA GGA        480
Ser Asp Ile Gly Ile Thr Ala Val Trp Ile Pro Pro Ala Tyr Lys Gly
                35                  40                  45

TTG AGC CAA TCC GAT AAC GGA TAC GGA CCT TAT GAT TTG TAT GAT TTA        528
Leu Ser Gln Ser Asp Asn Gly Tyr Gly Pro Tyr Asp Leu Tyr Asp Leu
            50                  55                  60

GGA GAA TTC CAG CAA AAA GGG ACG GTC AGA ACG AAA TAC GGC ACA AAA        576
Gly Glu Phe Gln Gln Lys Gly Thr Val Arg Thr Lys Tyr Gly Thr Lys
            65                  70                  75

TCA GAG CTT CAA GAT GCG ATC GGC TCA CTG CAT TCC CGG AAC GTC CAA        624
Ser Glu Leu Gln Asp Ala Ile Gly Ser Leu His Ser Arg Asn Val Gln
```

```
                80                   85                    90
GTA TAC GGA GAT GTG GTT TTG AAT CAT AAG GCT GGT GCT GAT GCA ACA        672
Val Tyr Gly Asp Val Val Leu Asn His Lys Ala Gly Ala Asp Ala Thr
 95              100                 105                 110

GAA GAT GTA ACT GCC GTC GAA GTC AAT CCG GCC AAT AGA AAT CAG GAA        720
Glu Asp Val Thr Ala Val Glu Val Asn Pro Ala Asn Arg Asn Gln Glu
                115                 120                 125

ACT TCG GAG GAA TAT CAA ATC AAA GCG TGG ACG GAT TTT CGT TTT CCG        768
Thr Ser Glu Glu Tyr Gln Ile Lys Ala Trp Thr Asp Phe Arg Phe Pro
            130                 135                 140

GGC CGT GGA AAC ACG TAC AGT GAT TTT AAA TGG CAT TGG TAT CAT TTC        816
Gly Arg Gly Asn Thr Tyr Ser Asp Phe Lys Trp His Trp Tyr His Phe
        145                 150                 155

GAC GGA GCG GAC TGG GAT GAA TCC CGG AAG ATC AGC CGC ATC TTT AAG        864
Asp Gly Ala Asp Trp Asp Glu Ser Arg Lys Ile Ser Arg Ile Phe Lys
    160                 165                 170

TTT CGT GGG GAA GGA AAA GCG TGG GAT TGG GAA GTA TCA AGT GAA AAC        912
Phe Arg Gly Glu Gly Lys Ala Trp Asp Trp Glu Val Ser Ser Glu Asn
175                 180                 185                 190

GGC AAC TAT GAC TAT TTA ATG TAT GCT GAT GTT GAC TAC GAC CAC CCT        960
Gly Asn Tyr Asp Tyr Leu Met Tyr Ala Asp Val Asp Tyr Asp His Pro
                195                 200                 205

GAT GTC GTG GCA GAG ACA AAA AAA TGG GGT ATC TGG TAT GCG AAT GAA       1008
Asp Val Val Ala Glu Thr Lys Lys Trp Gly Ile Trp Tyr Ala Asn Glu
                210                 215                 220

CTG TCA TTA GAC GGC TTC CGT ATT GAT GCC GCC AAA CAT ATT AAA TTT       1056
Leu Ser Leu Asp Gly Phe Arg Ile Asp Ala Ala Lys His Ile Lys Phe
            225                 230                 235

TCA TTT CTG CGT GAT TGG GTT CAG GCG GTC AGA CAG GCG ACG GGA AAA       1104
Ser Phe Leu Arg Asp Trp Val Gln Ala Val Arg Gln Ala Thr Gly Lys
        240                 245                 250

GAA ATG TTT ACG GTT GCG GAG TAT TGG CAG AAT AAT GCC GGG AAA CTC       1152
Glu Met Phe Thr Val Ala Glu Tyr Trp Gln Asn Asn Ala Gly Lys Leu
    255                 260                 265                 270

GAA AAC TAC TTG AAT AAA ACA AGC TTT AAT CAA TCC GTG TTT GAT GTT       1200
Glu Asn Tyr Leu Asn Lys Thr Ser Phe Asn Gln Ser Val Phe Asp Val
                275                 280                 285

CCG CTT CAT TTC AAT TTA CAG GCG GCT TCC TCA CAA GGA GGC GGA TAT       1248
Pro Leu His Phe Asn Leu Gln Ala Ala Ser Ser Gln Gly Gly Gly Tyr
                290                 295                 300

GAT ATG AGG CGT TTG CTG GAC GGT ACC GTT GTG TCC AGG CAT CCG GAA       1296
Asp Met Arg Arg Leu Leu Asp Gly Thr Val Val Ser Arg His Pro Glu
                305                 310                 315

AAG GCG GTT ACA TTT GTT GAA AAT CAT GAC ACA CAG CCG GGA CAG TCA       1344
Lys Ala Val Thr Phe Val Glu Asn His Asp Thr Gln Pro Gly Gln Ser
            320                 325                 330

TTG GAA TCG ACA GTC CAA ACT TGG TTT AAA CCG CTT GCA TAC GCC TTT       1392
Leu Glu Ser Thr Val Gln Thr Trp Phe Lys Pro Leu Ala Tyr Ala Phe
335                 340                 345                 350

ATT TTG ACA AGA GAA TCC GGT TAT CCT CAG GTG TTC TAT GGG GAT ATG       1440
Ile Leu Thr Arg Glu Ser Gly Tyr Pro Gln Val Phe Tyr Gly Asp Met
                355                 360                 365

TAC GGG ACA AAA GGG ACA TCG CCA AAG GAA ATT CCC TCA CTG AAA GAT       1488
Tyr Gly Thr Lys Gly Thr Ser Pro Lys Glu Ile Pro Ser Leu Lys Asp
            370                 375                 380

AAT ATA GAG CCG ATT TTA AAA GCG CGT AAG GAG TAC GCA TAC GGG CCC       1536
Asn Ile Glu Pro Ile Leu Lys Ala Arg Lys Glu Tyr Ala Tyr Gly Pro
                385                 390                 395

CAG CAC GAT TAT ATT GAC CAC CCG GAT GTG ATC GGA TGG ACG AGG GAA       1584
Gln His Asp Tyr Ile Asp His Pro Asp Val Ile Gly Trp Thr Arg Glu
```

```
                    400                 405                 410
GGT GAC AGC TCC GCC GCC AAA TCA GGT TTG GCC GCT TTA ATC ACG GAC      1632
Gly Asp Ser Ser Ala Ala Lys Ser Gly Leu Ala Ala Leu Ile Thr Asp
415                 420                 425                 430

GGA CCC GGC GGA TCA AAG CGG ATG TAT GCC GGC CTG AAA AAT GCC GGC      1680
Gly Pro Gly Gly Ser Lys Arg Met Tyr Ala Gly Leu Lys Asn Ala Gly
                    435                 440                 445

GAG ACA TGG TAT GAC ATA ACG GGC AAC CGT TCA GAT ACT GTA AAA ATC      1728
Glu Thr Trp Tyr Asp Ile Thr Gly Asn Arg Ser Asp Thr Val Lys Ile
                450                 455                 460

GGA TCT GAC GGC TGG GGA GAG TTT CAT GTA AAC GAT GGG TCC GTC TCC      1776
Gly Ser Asp Gly Trp Gly Glu Phe His Val Asn Asp Gly Ser Val Ser
            465                 470                 475

ATT TAT GTT CAG AAA TAAGGTAATA AAAAAACACC TCCAAGCTGA GTGCGGGTAT      1831
Ile Tyr Val Gln Lys
        480

CAGCTTGGAG GTGCGTTTAT TTTTTCAGCC GTATGACAAG GTCGGCATCA GGTGTGACAA    1891

ATACGGTATG CTGGCTGTCA TAGGTGACAA ATCCGGGTTT TGCGCCGTTT GGCTTTTTCA    1951

CATGTCTGAT TTTTGTATAA TCAACAGGCA CGGAGCCGGA ATCTTTCGCC TTGGAAAAAT    2011

AAGCGGCGAT CGTAGCTGCT TCCAATATGG ATTGTTCATC GGGATCGCTG CTTTTAATCA    2071

CAACGTGGGA TCC                                                      2084

(2) INFORMATION FOR SEQ ID NO:4:

(i) SEQUENCE CHARACTERISTICS:
        (A) LENGTH: 514 amino acids
        (B) TYPE: amino acid
        (D) TOPOLOGY: linear (ii) MOLECULE TYPE: protein (xi) SEQUENCE DESCRIPTION: SEQ ID NO:4:

Met Ile Gln Lys Arg Lys Arg Thr Val Ser Phe Arg Leu Val Leu Met
-31 -30                 -25                 -20

Cys Thr Leu Leu Phe Val Ser Leu Pro Ile Thr Lys Thr Ser Ala Val
-15                 -10                 -5                   1

Asn Gly Thr Leu Met Gln Tyr Phe Glu Trp Tyr Thr Pro Asn Asp Gly
                5                   10                  15

Gln His Trp Lys Arg Leu Gln Asn Asp Ala Glu His Leu Ser Asp Ile
            20                  25                  30

Gly Ile Thr Ala Val Trp Ile Pro Pro Ala Tyr Lys Gly Leu Ser Gln
        35                  40                  45

Ser Asp Asn Gly Tyr Gly Pro Tyr Asp Leu Tyr Asp Leu Gly Glu Phe
50                  55                  60                  65

Gln Gln Lys Gly Thr Val Arg Thr Lys Tyr Gly Thr Lys Ser Glu Leu
                70                  75                  80

Gln Asp Ala Ile Gly Ser Leu His Ser Arg Asn Val Gln Val Tyr Gly
            85                  90                  95

Asp Val Val Leu Asn His Lys Ala Gly Ala Asp Ala Thr Glu Asp Val
        100                 105                 110

Thr Ala Val Glu Val Asn Pro Ala Asn Arg Asn Gln Glu Thr Ser Glu
    115                 120                 125

Glu Tyr Gln Ile Lys Ala Trp Thr Asp Phe Arg Phe Pro Gly Arg Gly
130                 135                 140                 145

Asn Thr Tyr Ser Asp Phe Lys Trp His Trp Tyr His Phe Asp Gly Ala
                150                 155                 160
```

Asp Trp Asp Glu Ser Arg Lys Ile Ser Arg Ile Phe Lys Phe Arg Gly
                165                 170                 175

Glu Gly Lys Ala Trp Asp Trp Glu Val Ser Glu Asn Gly Asn Tyr
            180                 185                 190

Asp Tyr Leu Met Tyr Ala Asp Val Asp Tyr Asp His Pro Asp Val Val
195                 200                 205

Ala Glu Thr Lys Lys Trp Gly Ile Trp Tyr Ala Asn Glu Leu Ser Leu
210                 215                 220                 225

Asp Gly Phe Arg Ile Asp Ala Ala Lys His Ile Lys Phe Ser Phe Leu
                230                 235                 240

Arg Asp Trp Val Gln Ala Val Arg Gln Ala Thr Gly Lys Glu Met Phe
                245                 250                 255

Thr Val Ala Glu Tyr Trp Gln Asn Asn Ala Gly Lys Leu Glu Asn Tyr
                260                 265                 270

Leu Asn Lys Thr Ser Phe Asn Gln Ser Val Phe Asp Val Pro Leu His
275                 280                 285

Phe Asn Leu Gln Ala Ala Ser Ser Gln Gly Gly Gly Tyr Asp Met Arg
290                 295                 300                 305

Arg Leu Leu Asp Gly Thr Val Val Ser Arg His Pro Glu Lys Ala Val
                310                 315                 320

Thr Phe Val Glu Asn His Asp Thr Gln Pro Gly Gln Ser Leu Glu Ser
                325                 330                 335

Thr Val Gln Thr Trp Phe Lys Pro Leu Ala Tyr Ala Phe Ile Leu Thr
                340                 345                 350

Arg Glu Ser Gly Tyr Pro Gln Val Phe Tyr Gly Asp Met Tyr Gly Thr
355                 360                 365

Lys Gly Thr Ser Pro Lys Glu Ile Pro Ser Leu Lys Asp Asn Ile Glu
370                 375                 380                 385

Pro Ile Leu Lys Ala Arg Lys Glu Tyr Ala Tyr Gly Pro Gln His Asp
                390                 395                 400

Tyr Ile Asp His Pro Asp Val Ile Gly Trp Thr Arg Glu Gly Asp Ser
                405                 410                 415

Ser Ala Ala Lys Ser Gly Leu Ala Ala Leu Ile Thr Asp Gly Pro Gly
                420                 425                 430

Gly Ser Lys Arg Met Tyr Ala Gly Leu Lys Asn Ala Gly Glu Thr Trp
435                 440                 445

Tyr Asp Ile Thr Gly Asn Arg Ser Asp Thr Val Lys Ile Gly Ser Asp
450                 455                 460                 465

Gly Trp Gly Glu Phe His Val Asn Asp Gly Ser Val Ser Ile Tyr Val
                470                 475                 480

Gln Lys (2) INFORMATION FOR SEQ ID NO:5:

(i) SEQUENCE CHARACTERISTICS:
        (A) LENGTH: 1814 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: sig_peptide
        (B) LOCATION: 156..257

(ix) FEATURE:
        (A) NAME/KEY: CDS
        (B) LOCATION: 156..1802

(ix) FEATURE:
    (A) NAME/KEY: mat_peptide
    (B) LOCATION: 258..1802

(xi) SEQUENCE DESCRIPTION: SEQ ID NO:5:

```
AAATTCGATA TTGAAAACGA TTACAAATAA AAATTATAAT AGACGTAAAC GTTCGAGGGT          60

TTGCTCCCTT TTTACTCTTT TTATGCAATC GTTTCCCTTA ATTTTTTGGA AGCCAAACCG         120

TCGAATGTAA CATTTGATTA AGGGGGAAGG GCATT GTG CTA ACG TTT CAC CGC           173
                                     Val Leu Thr Phe His Arg
                                     -34             -30

ATC ATT CGA AAA GGA TGG ATG TTC CTG CTC GCG TTT TTG CTC ACT GTC          221
Ile Ile Arg Lys Gly Trp Met Phe Leu Leu Ala Phe Leu Leu Thr Val
            -25             -20             -15

TCG CTG TTC TGC CCA ACA GGA CAG CCC GCC AAG GCT GCC GCA CCG TTT          269
Ser Leu Phe Cys Pro Thr Gly Gln Pro Ala Lys Ala Ala Ala Pro Phe
        -10              -5                   1

AAC GGC ACC ATG ATG CAG TAT TTT GAA TGG TAC TTG CCG GAT GAT GGC          317
Asn Gly Thr Met Met Gln Tyr Phe Glu Trp Tyr Leu Pro Asp Asp Gly
  5               10                  15                  20

ACG TTA TGG ACC AAA GTG GCC AAT GAA GCC AAC AAC TTA TCC AGC CTT          365
Thr Leu Trp Thr Lys Val Ala Asn Glu Ala Asn Asn Leu Ser Ser Leu
                25                  30                  35

GGC ATC ACC GCT CTT TGG CTG CCG CCC GCT TAC AAA GGA ACA AGC CGC          413
Gly Ile Thr Ala Leu Trp Leu Pro Pro Ala Tyr Lys Gly Thr Ser Arg
            40                  45                  50

AGC GAC GTA GGG TAC GGA GTA TAC GAC TTG TAT GAC CTC GGC GAA TTC          461
Ser Asp Val Gly Tyr Gly Val Tyr Asp Leu Tyr Asp Leu Gly Glu Phe
            55                  60                  65

AAT CAA AAA GGG ACC GTC CGC ACA AAA TAC GGA ACA AAA GCT CAA TAT          509
Asn Gln Lys Gly Thr Val Arg Thr Lys Tyr Gly Thr Lys Ala Gln Tyr
    70                  75                  80

CTT CAA GCC ATT CAA GCC GCC CAC GCC GCT GGA ATG CAA GTG TAC GCC          557
Leu Gln Ala Ile Gln Ala Ala His Ala Ala Gly Met Gln Val Tyr Ala
 85                  90                  95                 100

GAT GTC GTG TTC GAC CAT AAA GGC GGC GCT GAC GGC ACG GAA TGG GTG          605
Asp Val Val Phe Asp His Lys Gly Gly Ala Asp Gly Thr Glu Trp Val
                105                 110                 115

GAC GCC GTC GAA GTC AAT CCG TCC GAC CGC AAC CAA GAA ATC TCG GGC          653
Asp Ala Val Glu Val Asn Pro Ser Asp Arg Asn Gln Glu Ile Ser Gly
            120                 125                 130

ACC TAT CAA ATC CAA GCA TGG ACG AAA TTT GAT TTT CCC GGG CGG GGC          701
Thr Tyr Gln Ile Gln Ala Trp Thr Lys Phe Asp Phe Pro Gly Arg Gly
            135                 140                 145

AAC ACC TAC TCC AGC TTT AAG TGG CGC TGG TAC CAT TTT GAC GGC GTT          749
Asn Thr Tyr Ser Ser Phe Lys Trp Arg Trp Tyr His Phe Asp Gly Val
    150                 155                 160

GAT TGG GAC GAA AGC CGA AAA TTG AGC CGC ATT TAC AAA TTC CGC GGC          797
Asp Trp Asp Glu Ser Arg Lys Leu Ser Arg Ile Tyr Lys Phe Arg Gly
165                 170                 175                 180

ATC GGC AAA GCG TGG GAT TGG GAA GTA GAC ACG GAA AAC GGA AAC TAT          845
Ile Gly Lys Ala Trp Asp Trp Glu Val Asp Thr Glu Asn Gly Asn Tyr
                185                 190                 195

GAC TAC TTA ATG TAT GCC GAC CTT GAT ATG GAT CAT CCC GAA GTC GTG          893
Asp Tyr Leu Met Tyr Ala Asp Leu Asp Met Asp His Pro Glu Val Val
            200                 205                 210

ACC GAG CTG AAA AAC TGG GGG AAA TGG TAT GTC AAC ACA ACG AAC ATT          941
Thr Glu Leu Lys Asn Trp Gly Lys Trp Tyr Val Asn Thr Thr Asn Ile
            215                 220                 225

GAT GGG TTC CGG CTT GAT GCC GTC AAG CAT ATT AAG TTC AGT TTT TTT          989
```

```
Asp Gly Phe Arg Leu Asp Ala Val Lys His Ile Lys Phe Ser Phe Phe
    230                 235                 240

CCT GAT TGG TTG TCG TAT GTG CGT TCT CAG ACT GGC AAG CCG CTA TTT       1037
Pro Asp Trp Leu Ser Tyr Val Arg Ser Gln Thr Gly Lys Pro Leu Phe
245                 250                 255                 260

ACC GTC GGG GAA TAT TGG AGC TAT GAC ATC AAC AAG TTG CAC AAT TAC       1085
Thr Val Gly Glu Tyr Trp Ser Tyr Asp Ile Asn Lys Leu His Asn Tyr
                265                 270                 275

ATT ACG AAA ACA GAC GGA ACG ATG TCT TTG TTT GAT GCC CCG TTA CAC       1133
Ile Thr Lys Thr Asp Gly Thr Met Ser Leu Phe Asp Ala Pro Leu His
            280                 285                 290

AAC AAA TTT TAT ACC GCT TCC AAA TCA GGG GGC GCA TTT GAT ATG CGC       1181
Asn Lys Phe Tyr Thr Ala Ser Lys Ser Gly Gly Ala Phe Asp Met Arg
        295                 300                 305

ACG TTA ATG ACC AAT ACT CTC ATG AAA GAT CAA CCG ACA TTG GCC GTC       1229
Thr Leu Met Thr Asn Thr Leu Met Lys Asp Gln Pro Thr Leu Ala Val
    310                 315                 320

ACC TTC GTT GAT AAT CAT GAC ACC GAA CCC GGC CAA GCG CTG CAG TCA       1277
Thr Phe Val Asp Asn His Asp Thr Glu Pro Gly Gln Ala Leu Gln Ser
325                 330                 335                 340

TGG GTC GAC CCA TGG TTC AAA CCG TTG GCT TAC GCC TTT ATT CTA ACT       1325
Trp Val Asp Pro Trp Phe Lys Pro Leu Ala Tyr Ala Phe Ile Leu Thr
                345                 350                 355

CGG CAG GAA GGA TAC CCG TGC GTC TTT TAT GGT GAC TAT TAT GGC ATT       1373
Arg Gln Glu Gly Tyr Pro Cys Val Phe Tyr Gly Asp Tyr Tyr Gly Ile
            360                 365                 370

CCA CAA TAT AAC ATT CCT TCG CTG AAA AGC AAA ATC GAT CCG CTC CTC       1421
Pro Gln Tyr Asn Ile Pro Ser Leu Lys Ser Lys Ile Asp Pro Leu Leu
        375                 380                 385

ATC GCG CGC AGG GAT TAT GCT TAC GGA ACG CAA CAT GAT TAT CTT GAT       1469
Ile Ala Arg Arg Asp Tyr Ala Tyr Gly Thr Gln His Asp Tyr Leu Asp
    390                 395                 400

CAC TCC GAC ATC ATC GGG TGG ACA AGG GAA GGG GGC ACT GAA AAA CCA       1517
His Ser Asp Ile Ile Gly Trp Thr Arg Glu Gly Gly Thr Glu Lys Pro
405                 410                 415                 420

GGA TCC GGA CTG GCC GCA CTG ATC ACC GAT GGG CCG GGA GGA AGC AAA       1565
Gly Ser Gly Leu Ala Ala Leu Ile Thr Asp Gly Pro Gly Gly Ser Lys
                425                 430                 435

TGG ATG TAC GTT GGC AAA CAA CAC GCT GGA AAA GTG TTC TAT GAC CTT       1613
Trp Met Tyr Val Gly Lys Gln His Ala Gly Lys Val Phe Tyr Asp Leu
            440                 445                 450

ACC GGC AAC CGG AGT GAC ACC GTC ACC ATC AAC AGT GAT GGA TGG GGG       1661
Thr Gly Asn Arg Ser Asp Thr Val Thr Ile Asn Ser Asp Gly Trp Gly
        455                 460                 465

GAA TTC AAA GTC AAT GGC GGT TCG GTT TCG GTT TGG GTT CCT AGA AAA       1709
Glu Phe Lys Val Asn Gly Gly Ser Val Ser Val Trp Val Pro Arg Lys
    470                 475                 480

ACG ACC GTT TCT ACC ATC GCT CGG CCG ATC ACA ACC CGA CCG TGG ACT       1757
Thr Thr Val Ser Thr Ile Ala Arg Pro Ile Thr Thr Arg Pro Trp Thr
485                 490                 495                 500

GGT GAA TTC GTC CGT TGG ACC GAA CCA CGG TTG GTG GCA TGG CCT           1802
Gly Glu Phe Val Arg Trp Thr Glu Pro Arg Leu Val Ala Trp Pro
                505                 510                 515

TGATGCCTGC GA                                                         1814

(2) INFORMATION FOR SEQ ID NO:6:

(i) SEQUENCE CHARACTERISTICS:
        (A) LENGTH: 549 amino acids
        (B) TYPE: amino acid
        (D) TOPOLOGY: linear
```

(ii) MOLECULE TYPE: protein (xi) SEQUENCE DESCRIPTION: SEQ ID NO:6:

```
Val Leu Thr Phe His Arg Ile Ile Arg Lys Gly Trp Met Phe Leu Leu
-34              -30                 -25                 -20

Ala Phe Leu Leu Thr Val Ser Leu Phe Cys Pro Thr Gly Gln Pro Ala
            -15                 -10                  -5

Lys Ala Ala Ala Pro Phe Asn Gly Thr Met Met Gln Tyr Phe Glu Trp
  1              5                  10

Tyr Leu Pro Asp Asp Gly Thr Leu Trp Thr Lys Val Ala Asn Glu Ala
 15              20                  25                  30

Asn Asn Leu Ser Ser Leu Gly Ile Thr Ala Leu Trp Leu Pro Pro Ala
             35                  40                  45

Tyr Lys Gly Thr Ser Arg Ser Asp Val Gly Tyr Gly Val Tyr Asp Leu
             50                  55                  60

Tyr Asp Leu Gly Glu Phe Asn Gln Lys Gly Thr Val Arg Thr Lys Tyr
             65                  70                  75

Gly Thr Lys Ala Gln Tyr Leu Gln Ala Ile Gln Ala Ala His Ala Ala
             80                  85                  90

Gly Met Gln Val Tyr Ala Asp Val Val Phe Asp His Lys Gly Gly Ala
 95              100                 105                 110

Asp Gly Thr Glu Trp Val Asp Ala Val Glu Val Asn Pro Ser Asp Arg
                115                 120                 125

Asn Gln Glu Ile Ser Gly Thr Tyr Gln Ile Gln Ala Trp Thr Lys Phe
                130                 135                 140

Asp Phe Pro Gly Arg Gly Asn Thr Tyr Ser Ser Phe Lys Trp Arg Trp
            145                 150                 155

Tyr His Phe Asp Gly Val Asp Trp Asp Glu Ser Arg Lys Leu Ser Arg
            160                 165                 170

Ile Tyr Lys Phe Arg Gly Ile Gly Lys Ala Trp Asp Trp Glu Val Asp
175             180                 185                 190

Thr Glu Asn Gly Asn Tyr Asp Tyr Leu Met Tyr Ala Asp Leu Asp Met
                195                 200                 205

Asp His Pro Glu Val Val Thr Glu Leu Lys Asn Trp Gly Lys Trp Tyr
            210                 215                 220

Val Asn Thr Thr Asn Ile Asp Gly Phe Arg Leu Asp Ala Val Lys His
            225                 230                 235

Ile Lys Phe Ser Phe Pro Asp Trp Leu Ser Tyr Val Arg Ser Gln
240             245                 250

Thr Gly Lys Pro Leu Phe Thr Val Gly Glu Tyr Trp Ser Tyr Asp Ile
255             260                 265                 270

Asn Lys Leu His Asn Tyr Ile Thr Lys Thr Asp Gly Thr Met Ser Leu
                275                 280                 285

Phe Asp Ala Pro Leu His Asn Lys Phe Tyr Thr Ala Ser Lys Ser Gly
            290                 295                 300

Gly Ala Phe Asp Met Arg Thr Leu Met Thr Asn Thr Leu Met Lys Asp
            305                 310                 315

Gln Pro Thr Leu Ala Val Thr Phe Val Asp Asn His Asp Thr Glu Pro
320                 325                 330

Gly Gln Ala Leu Gln Ser Trp Val Asp Pro Trp Phe Lys Pro Leu Ala
335                 340                 345                 350

Tyr Ala Phe Ile Leu Thr Arg Gln Glu Gly Tyr Pro Cys Val Phe Tyr
                355                 360                 365
```

```
Gly Asp Tyr Tyr Gly Ile Pro Gln Tyr Asn Ile Pro Ser Leu Lys Ser
            370                 375                 380

Lys Ile Asp Pro Leu Leu Ile Ala Arg Arg Asp Tyr Ala Tyr Gly Thr
            385                 390                 395

Gln His Asp Tyr Leu Asp His Ser Asp Ile Ile Gly Trp Thr Arg Glu
            400                 405                 410

Gly Gly Thr Glu Lys Pro Gly Ser Gly Leu Ala Ala Leu Ile Thr Asp
415                 420                 425                 430

Gly Pro Gly Gly Ser Lys Trp Met Tyr Val Gly Lys Gln His Ala Gly
                435                 440                 445

Lys Val Phe Tyr Asp Leu Thr Gly Asn Arg Ser Asp Thr Val Thr Ile
            450                 455                 460

Asn Ser Asp Gly Trp Gly Glu Phe Lys Val Asn Gly Gly Ser Val Ser
            465                 470                 475

Val Trp Val Pro Arg Lys Thr Thr Val Ser Thr Ile Ala Arg Pro Ile
480                 485                 490

Thr Thr Arg Pro Trp Thr Gly Glu Phe Val Arg Trp Thr Glu Pro Arg
495                 500                 505                 510

Leu Val Ala Trp Pro
                515

(2) INFORMATION FOR SEQ ID NO:7:

(i) SEQUENCE CHARACTERISTICS:
        (A) LENGTH: 1385 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

Ser Glu Arg Gly Leu Gly Leu Asn Ile Leu Glu Ala Ser Pro Ala Ser
1               5                   10                  15

Asn Ala Leu Ala Thr His Arg Pro Arg Ala Leu Ala Ala Ser Pro Thr
            20                  25                  30

Arg Pro Ala Arg Gly Ser Glu Arg Gly Leu Asn Ser Glu Arg Ile Leu
            35                  40                  45

Glu Thr Tyr Arg Pro His Glu Leu Glu Leu Glu Thr His Arg Ala Ser
    50                  55                  60

Pro Ala Arg Gly Pro His Glu Ala Leu Ala Ala Arg Gly Thr His Arg
65                  70                  75                  80

Ala Ser Pro Gly Leu Tyr Ser Glu Arg Thr His Arg Thr His Arg Ala
                85                  90                  95

Leu Ala Thr His Arg Cys Tyr Ser Ala Ser Asn Thr His Arg Ala Leu
                100                 105                 110

Ala Ala Ser Pro Gly Leu Asn Leu Tyr Ser Thr Tyr Arg Cys Tyr Ser
            115                 120                 125

Gly Leu Tyr Gly Leu Tyr Thr His Arg Thr Arg Pro Gly Leu Asn Gly
            130                 135                 140

Leu Tyr Ile Leu Glu Ile Leu Glu Ala Ser Pro Leu Tyr Ser Leu Glu
145                 150                 155                 160

Ala Ser Pro Thr Tyr Arg Ile Leu Glu Gly Leu Asn Gly Leu Tyr Met
                165                 170                 175

Glu Thr Gly Leu Tyr Pro His Glu Thr His Arg Ala Leu Ala Ile Leu
            180                 185                 190

Glu Thr Arg Pro Ile Leu Glu Thr His Arg Pro Arg Val Ala Leu Thr
```

-continued

```
                    195                 200                 205
His Arg Ala Leu Ala Gly Leu Asn Leu Glu Pro Arg Gly Leu Asn Thr
    210                 215                 220

His Arg Thr His Arg Ala Leu Ala Thr Tyr Arg Gly Leu Tyr Ala Ser
225                 230                 235                 240

Pro Ala Leu Ala Thr Tyr Arg His Ile Ser Gly Leu Tyr Thr Tyr Arg
                245                 250                 255

Thr Arg Pro Gly Leu Asn Gly Leu Asn Ala Ser Pro Ile Leu Glu Thr
                260                 265                 270

Tyr Arg Ser Glu Arg Leu Glu Ala Ser Asn Gly Leu Ala Ser Asn Thr
            275                 280                 285

Tyr Arg Gly Leu Tyr Thr His Arg Ala Leu Ala Ala Ser Pro Ala Ser
            290                 295                 300

Pro Leu Glu Leu Tyr Ser Ala Leu Ala Leu Glu Ser Glu Arg Ser Glu
305                 310                 315                 320

Arg Ala Leu Ala Leu Glu His Ile Ser Gly Leu Ala Arg Gly Gly Leu
                325                 330                 335

Tyr Met Glu Thr Thr Tyr Arg Leu Glu Met Glu Thr Val Ala Leu Ala
                340                 345                 350

Ser Pro Val Ala Leu Val Ala Leu Ala Leu Ala Ala Ser Asn His Ile
                355                 360                 365

Ser Met Glu Thr Gly Leu Tyr Thr Tyr Arg Ala Ser Pro Gly Leu Tyr
    370                 375                 380

Ala Leu Ala Gly Leu Tyr Ser Glu Arg Ser Glu Arg Val Ala Leu Ala
385                 390                 395                 400

Ser Pro Thr Tyr Arg Ser Glu Arg Val Ala Leu Pro His Glu Leu Tyr
                405                 410                 415

Ser Pro Arg Pro His Glu Ser Glu Arg Ser Glu Arg Gly Leu Asn Ala
                420                 425                 430

Ser Pro Thr Tyr Arg Pro His Glu His Ile Ser Pro Arg Pro His Glu
                435                 440                 445

Cys Tyr Ser Pro His Glu Ile Leu Glu Gly Leu Asn Ala Ser Asn Thr
    450                 455                 460

Tyr Arg Gly Leu Ala Ser Pro Gly Leu Asn Thr His Arg Gly Leu Asn
465                 470                 475                 480

Val Ala Leu Gly Leu Ala Ser Pro Cys Tyr Ser Thr Arg Pro Leu Glu
                485                 490                 495

Gly Leu Tyr Ala Ser Pro Ala Ser Asn Thr His Arg Val Ala Leu Ser
                500                 505                 510

Glu Arg Leu Glu Pro Arg Ala Ser Pro Leu Glu Ala Ser Pro Thr His
                515                 520                 525

Arg Thr His Arg Leu Tyr Ser Ala Ser Pro Val Ala Leu Val Ala Leu
    530                 535                 540

Leu Tyr Ser Ala Ser Asn Gly Leu Thr Arg Pro Thr Tyr Arg Ala Ser
545                 550                 555                 560

Pro Thr Arg Pro Val Ala Leu Gly Leu Tyr Ser Glu Arg Leu Glu Val
                565                 570                 575

Ala Leu Ser Glu Arg Ala Ser Asn Thr Tyr Arg Ser Glu Arg Ile Leu
                580                 585                 590

Glu Ala Ser Pro Gly Leu Tyr Leu Glu Ala Arg Gly Ile Leu Glu Ala
                595                 600                 605

Ser Pro Thr His Arg Val Ala Leu Leu Tyr Ser His Ile Ser Val Ala
                610                 615                 620
```

-continued

Leu Gly Leu Asn Leu Tyr Ser Ala Ser Pro Pro His Glu Thr Arg Pro
625                 630                 635                 640

Pro Arg Gly Leu Tyr Thr Tyr Arg Ala Ser Asn Leu Tyr Ser Ala Leu
            645                 650                 655

Ala Ala Leu Ala Gly Leu Tyr Val Ala Leu Thr Tyr Arg Cys Tyr Ser
            660                 665                 670

Ile Leu Glu Gly Leu Tyr Gly Leu Val Ala Leu Leu Glu Ala Ser Pro
            675                 680                 685

Gly Leu Tyr Ala Ser Pro Pro Arg Ala Leu Ala Thr Tyr Arg Thr His
    690                 695                 700

Arg Cys Tyr Ser Pro Arg Thr Tyr Arg Gly Leu Asn Ala Ser Asn Val
705                 710                 715                 720

Ala Leu Met Glu Thr Ala Ser Pro Gly Leu Tyr Val Ala Leu Leu Glu
            725                 730                 735

Ala Ser Asn Thr Tyr Arg Pro Arg Ile Leu Glu Thr Tyr Arg Thr Tyr
            740                 745                 750

Arg Pro Arg Leu Glu Leu Glu Ala Ser Asn Ala Leu Ala Pro His Glu
    755                 760                 765

Leu Tyr Ser Ser Glu Arg Thr His Arg Ser Glu Arg Gly Leu Tyr Ser
    770                 775                 780

Glu Arg Met Glu Thr Ala Ser Pro Ala Ser Pro Leu Glu Thr Tyr Arg
785                 790                 795                 800

Ala Ser Asn Met Glu Thr Ile Leu Glu Ala Ser Asn Thr His Arg Val
            805                 810                 815

Ala Leu Leu Tyr Ser Ser Glu Arg Ala Ser Pro Cys Tyr Ser Pro Arg
            820                 825                 830

Ala Ser Pro Ser Glu Arg Thr His Arg Leu Glu Leu Glu Gly Leu Tyr
            835                 840                 845

Thr His Arg Pro His Glu Val Ala Leu Gly Leu Ala Ser Asn His Ile
    850                 855                 860

Ser Ala Ser Pro Ala Ser Asn Pro Arg Ala Arg Gly Pro His Glu Ala
865                 870                 875                 880

Leu Ala Ser Glu Arg Thr Tyr Arg Thr His Arg Ala Ser Asn Ala Ser
            885                 890                 895

Pro Ile Leu Glu Ala Leu Ala Leu Glu Ala Leu Ala Leu Tyr Ser Ala
    900                 905                 910

Ser Asn Val Ala Leu Ala Leu Ala Ala Leu Ala Pro His Glu Ile Leu
    915                 920                 925

Glu Ile Leu Glu Leu Glu Ala Ser Asn Ala Ser Pro Gly Leu Tyr Ile
    930                 935                 940

Leu Glu Pro Arg Ile Leu Glu Ile Leu Glu Thr Tyr Arg Ala Leu Ala
945                 950                 955                 960

Gly Leu Tyr Gly Leu Asn Gly Leu Gly Leu Asn His Ile Ser Thr Tyr
            965                 970                 975

Arg Ala Leu Ala Gly Leu Tyr Gly Leu Tyr Ala Ser Asn Ala Ser Pro
            980                 985                 990

Pro Arg Ala Leu Ala Ala Ser Asn Ala Arg Gly Gly Leu Ala Leu Ala
            995                 1000                1005

Thr His Arg Thr Arg Pro Leu Glu Ser Glu Arg Gly Leu Tyr Thr Tyr
    1010                1015                1020

Arg Pro Arg Thr His Arg Ala Ser Pro Ser Glu Arg Gly Leu Leu Glu
1025                1030                1035                1040

Thr Tyr Arg Leu Tyr Ser Leu Glu Ile Leu Glu Ala Leu Ala Ser Glu
            1045                1050                1055

```
Arg Ala Leu Ala Ala Ser Asn Ala Leu Ala Ile Leu Glu Ala Arg Gly
            1060                1065                1070

Ala Ser Asn Thr Tyr Arg Ala Leu Ala Ile Leu Glu Ser Glu Arg Leu
            1075                1080                1085

Tyr Ser Ala Ser Pro Thr His Arg Gly Leu Tyr Pro His Glu Val Ala
            1090                1095                1100

Leu Thr His Arg Thr Tyr Arg Leu Tyr Ser Ala Ser Asn Thr Arg Pro
1105                1110                1115                1120

Pro Arg Ile Leu Glu Thr Tyr Arg Leu Tyr Ser Ala Ser Pro Ala Ser
            1125                1130                1135

Pro Ile Leu Glu Thr His Arg Ile Leu Glu Ala Leu Ala Met Glu Thr
            1140                1145                1150

Ala Arg Gly Leu Tyr Ser Gly Leu Tyr Thr His Arg Ala Ser Pro Gly
            1155                1160                1165

Leu Tyr Ser Glu Arg Gly Leu Asn Ile Leu Glu Val Ala Leu Thr His
            1170                1175                1180

Arg Ile Leu Glu Leu Glu Ser Glu Arg Ala Ser Asn Leu Tyr Ser Gly
1185                1190                1195                1200

Leu Tyr Ala Leu Ala Ser Glu Arg Gly Leu Tyr Ala Ser Pro Ser Glu
            1205                1210                1215

Arg Thr Tyr Arg Thr His Arg Leu Glu Ser Glu Arg Leu Glu Ser Glu
            1220                1225                1230

Arg Gly Leu Tyr Ala Leu Ala Gly Leu Tyr Thr Tyr Arg Thr His Arg
            1235                1240                1245

Ala Leu Ala Gly Leu Tyr Gly Leu Asn Gly Leu Asn Leu Glu Thr His
            1250                1255                1260

Arg Gly Leu Val Ala Leu Ile Leu Glu Gly Leu Tyr Cys Tyr Ser Thr
1265                1270                1275                1280

His Arg Thr His Arg Val Ala Leu Thr His Arg Val Ala Leu Gly Leu
            1285                1290                1295

Tyr Ser Glu Arg Ala Ser Pro Gly Leu Tyr Ala Ser Asn Val Ala Leu
            1300                1305                1310

Pro Arg Val Ala Leu Pro Arg Met Glu Thr Ala Leu Ala Gly Leu Tyr
            1315                1320                1325

Gly Leu Tyr Leu Glu Pro Arg Ala Arg Gly Val Ala Leu Leu Glu Thr
            1330                1335                1340

Tyr Arg Pro Arg Thr His Arg Gly Leu Leu Tyr Ser Leu Glu Ala Leu
1345                1350                1355                1360

Ala Gly Leu Tyr Ser Glu Arg Leu Tyr Ser Ile Leu Glu Cys Tyr Ser
            1365                1370                1375

Ser Glu Arg Ser Glu Arg Ser Glu Arg
            1380                1385
```

USE OF AN α-AMYLASE MODIFIED TO IMPROVE OXIDATION STABILITY IN A COMBINED DESIZING AND BLEACHING PROCESS

CROSS-REFERENCE TO RELATED APPLICATIONS

This application is a 35 U.S.C. 371 national application of PCT/DK94/00371 filed Oct. 5, 1994, which is incorporated herein by reference.

FIELD OF THE INVENTION

The present invention relates to a process for simultaneously desizing and bleaching of a fabric comprising starch or starch-derivatives as well as to the use of an oxidation stable α-amylase for said process.

BACKGROUND OF THE INVENTION

In the textile processing industry, α-amylases are traditionally used as auxiliaries in the desizing process to facilitate the removal of starch-containing size which has served as a protective coating on yarns during weaving.

Complete removal of the size coating after weaving is important to ensure optimum results in the subsequent processes, in which the fabric is generally scoured, bleached and dyed. Enzymatic starch break-down is preferred because it does not involve any harmful effect on the fibre material.

In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional α-amylases are not very compatible with high pH levels and bleaching agents. Alternatively, unrealistic high amounts of α-amylases, optionally in protected form, have to be used for such combined processes. The non-enzymatic breakdown of the starch size does lead to some fibre damage because of the rather aggressive chemicals used.

Accordingly, it would be desirable to use α-amylase enzymes having an improved resistance towards or being compatible with oxidation (bleaching) agents at elevated pH, in order to retain the advantages of enzymatic size break down in a time-saving and environmentally desirable simultaneous desizing and bleaching process.

U.S. Pat. No. 4,643,736 discloses a process for desizing and bleaching performed in a single operation, in which sodium chlorite is used in combination with a strong base, a surface active agent, an activator, and an amylolytic enzyme. However, the use of sodium chlorite is undesirable from an environmental point of view.

EP 119 920 discloses a process for simultaneous desizing and bleaching, in which sodium tetraborate decahydrate is used as buffer in a bath containing hydrogen peroxide, a sequestering agent, an amylase and a surfactant.

In both of the processes described in the above patent publications a relatively high amount of α-amylase is used, presumably in order to compensate for the low oxidation stability of the α-amylases used.

PCT/DK93/00230 discloses α-amylase mutants having improved oxidation stability. The mutants are indicated to be useful for desizing, but their use in a combined desizing and bleaching process is not mentioned.

BRIEF DISCLOSURE OF THE INVENTION

The fact that oxidation stable α-amylases now, for the first time, are available makes it possible to perform a combined enzymatic desizing and bleaching treatment of starch-containing fabrics. Accordingly, in a first aspect the invention relates to a process for simultaneously desizing and bleaching of a sized fabric containing starch or starch derivatives, which process comprises treating the fabric with a bleaching composition and an oxidation stable α-amylase.

It is contemplated that the use of oxidation stable α-amylases in the above process constitute an environmentally desirable alternative to non-enzymatic alkali or oxidation agents used today for desizing and bleaching. Furthermore, the oxidation stable α-amylase may be used in amounts corresponding to the amounts of α-amylase used in today's desizing processes.

In the present context, the term "oxidation stable" is intended to indicate that under conditions prevailing during the combined process of the invention, the oxidation stable α-amylase performs better than the *B. licheniformis* α-amylase, commercially available from the Applicant under the trade name Termamyl®. Termamyl® is presently considered to be highly useful for desizing, but is less suitable for a combined process due to a relatively low tolerance towards bleaching agents normally used for bleaching. The better performance may, e.g., be measured as described in the section entitled "Determination of oxidation stability" hereinafter.

The term "desizing" is intended to be understood in a conventional manner, i.e. the removal of size from the fabric, the term "scouring" the removal of non-cellulosic materials such as grease, wax, protein, hemi-cellulosic material, pectin, ash, dirt and oil, and term "bleaching" the bleaching of coloured impurities associated with the fibers of the fabric.

The term "simultaneously" is intended to indicate that the desizing and bleaching are carried out in a single operation. This has the obvious advantage that the washing and other treatments normally performed between separately conducted desizing and bleaching steps are no longer required. Thereby, the water and energy demand as well as the demand to different equipment to be used for each of the processes are considerably reduced. Furthermore, depending on the type of fabric to be treated and the nature of impurities present thereon, a scouring effect may be obtained during the performance of the process of the invention. Thus, in such cases, no additional scouring treatment need to be performed.

The term "fabric containing starch or starch derivatives" is intended to indicate any type of fabric, in particular woven fabric prepared from a cellulose-containing material, containing starch or starch derivatives. The fabric is normally made of cotton, viscose, flax and the like. The main part of the starch or starch derivatives present on the fabric is normally size with which the yarns, normally warp yarns, have been coated prior to weaving. In the present context, the term "fabric" is also intended to include garments and other types of processed fabrics.

In a second aspect the invention relates to a composition to be used in a simultaneous desizing and bleaching process, which composition comprises an oxidation stable α-amylase in combination with at least one further component selected from the group consisting of wetting agents, dispersing agents, sequestering agents and emulsifying agents.

In a final aspect the invention relates to the use of an oxidation stable α-amylase for a simultaneous desizing and bleaching process.

DETAILED DISCLOSURE OF THE INVENTION

The oxidation stable α-amylase

A preferred example of an α-amylase to be used in the process of the invention is one which has been prepared from a parent α-amylase by replacing one or more methionine residues of the parent α-amylase with any amino acid residue different from Cys or Met. Thus, according to the invention the amino acid residues to replace the methionine amino acid residue are the following: Ala, Arg, Asn, Asp, Gln, Glu, Gly, His, Ile, Leu, Lys, Phe, Pro, Ser, Thr, Trp, Tyr, and Val.

It has surprisingly been found that the mutant α-amylases prepared as described above exhibit a better activity level and a better stability in the presence of oxidizing agents than prior art mutant amylases.

It is preferred that the oxidation stable α-amylase to be used in the present process is of microbial origin. More particularly, it is preferred that the α-amylase is derivable from a strain of Bacillus. Thus, Bacillus α-amylases exhibit in themselves a high heat stability, and by being mutated as described above, the mutants may exhibit an even better stability, especially in the presence of oxidizing agents.

In the present context the term "derivable" is intended not only to indicate an α-amylase produced by a strain of the organism in question, but also an α-amylase encoded by a DNA sequence isolated from such strain and produced in a host organism transformed with said DNA sequence. Furthermore, the term is intended to indicate an α-amylase which is encoded by a DNA sequence of synthetic and/or cDNA origin and which has the identifying characteristics of the α-amylase in question.

Examples of parent Bacillus α-amylases useful for the present purpose are those derivable from a strain of *B. licheniformis*, a strain of *B. amyloliquefaciens*, or a strain of *B. stearothermophilus*.

The amino acid sequence for a *B. licheniformis* α-amylase useful for the present purpose is apparent from SEQ ID No. 2 (the corresponding DNA sequence is shown in SEQ ID No. 1). G. L. Gray et al., J. Bacteriol. 166, 635–643, 1986, FR 2665178 and EP 410 498 disclose variants of said α-amylase. The methionine numbers of the *B. licheniformis* α-amylase are: 8, 15, 197, 256, 304, 366, and 438.

The amino acid sequence for a *B. amyloliquefaciens* α-amylase useful for the present purpose is apparent from SEQ ID No. 4 (the corresponding DNA sequence is shown in SEQ ID No. 3). Takkinen et al., J. Biol. Chem. 258, 1007–1013, 1983 discloses a variant of said α-amylase. The methionine numbers of these *B. amyloliquefaciens* α-amylases are: 6, 197, 256, 304, 366, and 438.

The amino acid sequence for a *B. stearothermophilus* α-amylase useful for the present purpose is apparent from SEQ ID No. 6 (the corresponding DNA sequence is shown in SEQ ID No. 5). G. L. Gray et al., J. Bacteriol. 166, 635–643, 1986 disclose a variant of said α-amylase. The methionine numbers of these *B. stearothermophilus* α-amylases are: 8, 9, 97, 200, 206, 284, 307, 311, 316, and 437.

Furthermore, a parent α-amylase of fungal origin may be used, e.g. an α-amylase derivable from a strain of the fungal genus Aspergillus. For instance, the parent α-amylase may be derivable from a strain of the fungal species *A. oryzae* or *A. niger*. These α-amylases are all well characterized and their entire amino acid sequence is described.

The amino acid sequence for the *Asp. oryzae* α-amylase (sold commercially as FUNGAMYL®, by Novo Nordisk A/S) is shown in SEQ ID No. 7. The amino acid sequence of an *A. niger* α-amylase is shown in DK 5126/87.

In a preferred embodiment the parent α-amylase is selected from the group consisting of a *B. licheniformis, B. amyloliquefaciens, B. stearothermophilus, A. oryzae* and *A. niger* α-amylase, or is a functional analogue of any of said parent α-amylases which i) comprises an amino acid sequence being at least 60% homologous with the amino acid sequence of the parent α-amylase, ii) reacts with an antibody raised against the parent α-amylase, and/or iii) is encoded by a DNA sequence which hybridizes with the same probe as a DNA sequence encoding the parent α-amylase.

Property i) of the analogue is intended to indicate the degree of identity between the analogue and the parent α-amylase indicating a derivation of the first sequence from the second. In particular, a polypeptide is considered to be homologous to the parent α-amylase if a comparison of the respective amino acid sequences reveals an identity of greater than about 60%, such as above 70%, 80%, 85%, 90% or even 95%. Sequence comparisons can be performed via known algorithms, such as the one described by Lipman and Pearson (1985).

The homologous α-amylase may be a genetically engineered α-amylase, e.g. prepared in order to improve one or more properties such as thermostability, acid/alkaline stability, temperature or pH optimum and the like.

The additional properties ii) and iii) of the analogue of the parent α-amylase may be determined as follows:

Property ii), i.e. the immunological cross reactivity, may be assayed using an antibody raised against or reactive with at least one epitope of the parent α-amylase. The antibody, which may either be monoclonal or polyclonal, may be produced by methods known in the art, e.g. as described by Hudson et al., 1989. The immunological cross-reactivity may be determined using assays known in the art, examples of which are Western Blotting or radial immunodiffusion assay, e.g. as described by Hudson et al., 1989. In this respect, immunological cross-reactivity between parent *B. licheniformis, B. amyloliquefaciens* and *B. stearothermophilus* α-amylases having the amino acid sequences SEQ ID Nos. 2, 4 and 6, respectively, have been found.

The oligonucleotide probe used in the characterization of the analogue in accordance with property iii) defined above, may suitably be prepared on the basis of the full or partial nucleotide or amino acid sequence of the parent α-amylase. The hybridization may be carried out under any suitable conditions allowing the DNA sequences to hybridize. For instance, such conditions are hybridization under specified conditions, e.g. involving presoaking in 5×SSC and prehybridizing for 1 h at ~40° C. in a solution of 20% formamide, 5×Denhardt's solution, 50 mM sodium phosphate, pH 6.8, and 50 µg of denatured sonicated calf thymus DNA, followed by hybridization in the same solution supplemented with 100 µM ATP for 18 h at ~40° C., or other methods described by e.g. Sambrook et al., 1989.

Specific examples of analogues of the *B. licheniformis* α-amylase comprising the amino acid sequence shown in SEQ ID No. 2 are Termamyl® (available from Novo Nordisk A/S), Optitherm® and Takatherm® (available from Solvay), Maxamyl® (available from Gist-Brocades), Spezym AA® (available from Genencor), and Keistase® (available from Daiwa).

Specific examples of analogues of the *B. amyloliquefaciens* α-amylase comprising the amino acid sequence shown in SEQ ID No. 4 are BAN® (available from Novo Nordisk A/S), Optiamyls® (available from Solvay), Dexlo® and Rapidase® (available from Gist-Brocades), Kazuzase® (a mixed α-amylase and protease product available from Showa Denko).

Specific examples of analogues of the *B. stearothermophilus* α-amylase comprising the amino acid sequence shown in SEQ ID No. 6 are Liquozyme 280L® (available from Novo Nordisk A/S) and G-zyme 995® (available from Enzyme BioSystems).

In a preferred embodiment of the process of the invention the oxidation stable α-amylase is prepared from a parent α-amylase by replacing one or more of the methionine amino acid residues with a Leu, Thr, Ala, Gly, Ser, Ile, Asn, or Asp amino acid residue, preferably a Leu, Thr, Ala, or Gly amino acid residue.

In the present context, a mutant α-amylase of particular interest is one, in which the methionine amino acid residue in position 197 in *B. licheniformis* α-amylase or the methionine amino acid residue in homologous positions in other α-amylases is exchanged. The concept of homologous positions or sequence homology of α-amylases has been explained e.g. in Nakajima, R. et al., 1986, Appl. Microbiol. Biotechnol. 23, 355–360 and Liisa Holm et al., 1990, Protein Engineering 3, 181–191. Sequence homology of Bacillus α-amylases from *B. licheniformis, B. stearothermophilus* and *B. amyloliquefaciens* are about 60%. This makes it possible to align the sequences in order to compare residues at homologous positions in the sequence. By such alignment of α-amylase sequences the number in each α-amylase sequence of the homologous residues can be found. The homologous positions will probably spatially be in the same position in a three dimensional structure (Greer, J., 1981, J. Mol. Biol. 153, 1027–1042), thus having analogous impact on specific functions of the enzyme in question. In relation to position 197 in *B. licheniformis* α-amylase the homologous positions in *B. stearothermophilus* α-amylase are positions 200 and 206, and the homologous position in *B. amyloliquefaciens* α-amylase is position 197. Experimentally it has been found that these mutants exhibit both an improved activity level and an improved stability in the presence of oxidizing agents.

Accordingly, another type of oxidation stable α-amylases of interest for the present purpose, is an oxidation stable α-amylase prepared by replacing one or both of the methionine amino acid residues in positions 200 and 206 in a parent *B. stearothermophilus* α-amylase or the methionine amino acid residues in homologous positions in other α-amylases with other amino acid residues as explained above.

The mutant α-amylases disclosed above may be constructed in accordance with established methods, e.g. by use of site-directed mutagenesis.

Process conditions

It will be understood that the combined process of the invention may be performed in accordance with any suitable desizing or bleaching process known in the art, e.g. as described by Olson, E. S. "Textile Wet Processes, Vol. I, Noyes Publication, Park Ridge, N.J., USA (1983), M. Peter und H. K. Rouette, Grundlagen der Textilveredlung, Deutsche Fachverlag GmbH, Frankfurt am Main, Germany (1988). Thus, the process conditions to be used in performing the present invention may be selected so as to match a particular equipment or a particular type of process which it is desirable to use. Preferred examples of process types to be used in connection with the present invention include Jigger/Winch, Pad-Roll and Pad-Steam types. These types are dealt with in further detail below.

The combined process of the invention may be carried out as a batch, semi-continuous or continuous process using steam or the principles of cold-bleaching. As an example the process may comprise the following steps:

(a) Impregnating the fabric in a desizing and bleaching bath containing (as a minimum) an oxidation stable α-amylase and a bleaching agent followed by squeezing out excessive liquid so as to maintain the quantity of liquor necessary for the reaction to be carried out (normally between 60 and 120% of the weight of the dry fabric), (b) subjecting the impregnated fabric to steaming so as to bring the fabric to the desired reaction temperature, generally between 20° and 120° C., and (c) holding by rolling up or pleating the cloth in a J-Box, U-Box, carpet machine or the like for a sufficient period of time (normally between a few minutes and several hours) to allow the desizing and bleaching to occur.

As mentioned above, scouring may be an inherent result obtained when performing the combined process of the invention. However, for certain types of fabric it may be advantageous and/or necessary to subject the fabric to a scouring treatment in order to obtain a final product of a desired quality. In such cases, oxidation stable α-amylases disclosed herein may be employed in a combined desizing and scouring process, in particular oxidation stable α-amylases which are sufficiently stable at the high pH values, at which scouring is normally performed. Typically, a combined desizing and scouring process is carried out using a sufficient amount of an oxidation stable α-amylase and a strong alkali, such as NaOH, under conditions known in the art for desizing and scouring to be performed. Subsequently, the fabric resulting from a combined desizing and scouring treatment may be subjected to bleaching.

Normally, the oxidation stable α-amylase and the bleaching composition are added separately to the equipment in which the combined process is to take place. However, the oxidation stable α-amylase may also be mixed with the bleaching composition immediately prior to the combined treatment to be performed.

Although any type of bleaching agent may be used (such as sodium chlorite, sodium hypo chlorit and hydrogen peroxide) in the process of the invention it is preferred that a hydrogen peroxide based bleaching composition is used. Hydrogen peroxide constitutes the most gentle and environmentally friendly bleaching agent available today. The hydrogen peroxide is normally used in the form of a 35% solution and in an amount of 1–50 g/l of bleaching bath liquid, such as in an amount of 5–40 g/l, 5–30 g/l, 10–30 g/l or 30–40 g/l depending on the type of process to be used.

Further components required for the process to be performed are typically added separately. Examples of such components include a stabilizer and a wetting agent. The stabilizer may be an agent stabilizing the hydrogen peroxide (such as water glass ($Na_2O:SiO_2$) and a Magnesium salt) so as to control the reactivity of the hydrogen peroxide.

The wetting agent serves to improve the wettability of the fibre whereby a rapid and even desizing and bleaching may be obtained. The wetting agent is preferably of an oxidation stable type.

In a preferred embodiment of the process of the invention, the oxidation stable α-amylase is used in an amount exceeding 1 g/l, preferably in an amount of 1–20 g/l, such as 1–10 g/l, 1–5 g/l or 1–3 g/l. It will be understod that the amount of α-amylase to be used depend on the formulation of the α-amylase product in question.

Irrespective of the particular type of process to be used for the combined desizing and bleaching of the invention, the combined process is normally performed at a temperature in the range of 30–100° C., such as 50–100° C., 80–100° C., 90–100° C. or 90–95° C. and a pH in the range of 6.5–11, such as 9–10.8 or 10.0–10.8 . However, the actual process conditions may vary widely within these ranges as will be apparent from the following disclosure.

Preferred examples of the process conditions to be used in connection with the present invention include:

A batch type process, e.g. of the Jigger/Winch type, using

1–5 g/l of an oxidation stable α-amylase,

6–25 g/l of hydrogen peroxide (35%),

7–14 g/l of stabilizer, e.g. water glass, 0.25–5 g/l of a wetting agent, e.g. Arbyl R, available from Grünau, Germany, the process being performed at a pH in the range of 10–11 (obtained by addition of NaOH) and a temperature in the range of 90–95° C. (obtained by steaming), typically for 1–2 hours.

A semi-continuous process, e.g. of the Pad-Roll type, using

1–5 g/l of an oxidation stable α-amylase,

30–40 g/l of hydrogen peroxide (35%),

12–30 g/l of stabilizer, e.g. water glass, 0.25–5 g/l of a wetting agent, e.g. Arbyl R, the process being performed at a pH in the range of 10–11 (obtained by addition of NaOH) and a temperature in the range of 20–40° C., typically for 12–24 hours.

A continuous process, e.g. of the Pad-Steam type, using

1–5 g/l of an oxidation stable α-amylase,

8–25 g/l of hydrogen peroxide (35%),

5–20 g/l of stabilizer, e.g. water glass, 0.25–5 g/l of a wetting agent, e.g. Arbyl R, the process being performed at a pH in the range of 10–11 (obtained by addition of NaOH) and a temperature in the range of 98–140° C. (steaming), the temperature above 115 preferably being maintained for a few seconds only and the process time typically being 0.5–3 min.

It will be understood that the combined process may be performed in any equipment sufficiently tolerant towards the conditions of the process.

Furthermore, it will be evident that in addition to the oxidation stability of the α-amylase to be used in the process of the invention this amylase should preferably be one which is active at a pH of above 6.5, such as above 9.0. Preferably the oxidation stable α-amylase has a high activity in the pH range of 10–10.8.

Composition of the invention

Although the oxidation stable α-amylase may be added as such it is preferred that it is formulated into a suitable composition. Thus, the oxidation stable α-amylase may be used in the form of a granulate, preferably a non-dusting granulate, a liquid, in particular a stabilized liquid, a slurry, or in a protected form. Dust free granulates may be produced, e.g. as disclosed in U.S. Pat. No. 4,106,991 and U.S. Pat. No. 4,661,452 (both to Novo Nordisk A/S) and may optionally be coated by methods known in the art.

Liquid enzyme preparations may, for instance, be stabilized by adding a polyol such as e.g. propylene glycol, a sugar or sugar alcohol or acetic acid, according to established methods. Other enzyme stabilizers are well known in the art. Protected enzymes may be prepared according to the method disclosed in EP 238 216.

In principle the composition of the invention comprising an oxidation stable α-amylase may contain any other agent to be used in the combined process of the invention. However, it is preferred that the composition is free from the bleaching agent and other highly oxidizing agents.

The composition of the invention comprises at least one further component selected from the group consisting of wetting agents, dispersing agents, sequestering agents and emulsifying agents. Examples of suitable wetting agents are disclosed above. The emulsifying agent serves to emulsify hydrophobic impurities present on the fabric. The dispersing agent serves to prevent that extracted impurities redeposit on the fabric. The sequestering agent serve to remove ions such as Ca, Mg and Fe, which may have a negative impact on the process and preferred examples include caustic soda (sodium hydroxide) and soda ash (sodium carbonate).

Determination of oxidation stability

The amylase preparation is diluted to an amylase activity of 100 NU/ml (the NU (or KNU which is 1000 NU) amylase activity assay is defined in AF 207/1, which is available on request from Novo Nordisk A/S, and the unit is defined as follows: 1 KNU is the amount of enzyme which, per hour, under standard conditions, dextrinized 5.26 g starch dry substance Merch Amylum solubile, cat. no. 1253) in 50 mM of a Britton-Robinson buffer at pH 6–10 and incubated at 40–90° C. Subsequently $H_2O_2$ (35%) is added to a concentration of 1–50 g/l, and the pH value is readjusted to the desired value. the activity is now measured after 15 seconds and after 5, 15, and 30 minutes, the activities are determined as described in AF 207/1 but with a standard curve constructed at the chosen pH and temperature instead of at pH 7.3, 37° C. the results are compared to measurements of a preparation of Termamyl® (available from Novo Nordisk A/S, Denmark) under the same conditions.

The following non-limiting examples illustrates the invention.

EXAMPLE 1

Comparison of the pH-profile of oxidation stable α-amylase and conventional amylase Materials and methods Textile:
100% pure cotton, unbleached, 5 cm×5 cm swatches.

Enzymes:
A: *Bacillus licheniformis* oxidation stable α-amylase (methionin 197 replaced with leucin, activity 6.2 $KNU_p$/g, prepared by the Applicant, batch A943043K).

B: *Bacillus licheniformis* α-amylase (Termamyl 120L, activity 142 $KNU_p$/g, commercially available from the Applicant, batch AXR 4025 94-3).

Dosage: 30 $KNU_p$ enzyme/100 ml buffer.

Buffer: Britton-Robinson, pH 7 to 11

Dosage: 100 ml buffer/shake flask 100 ml buffer was added to a shake flask and placed in a heated water bath at 85° C. When the buffer had reached the temperature of 85° C., the enzyme preparation (A or B, respectively) was added together with one swatch. The swatches were treated in a shaking waterbath for 20 minutes at 85° C.

After the enzyme treatment the swatches were washed at 95° C. in 100 ml water containing 2 g of Kieralon CD/liter (a surfactant), followed by rinsing 4 times, each time in 100 ml cold deionized water. Then, the swatches were dried at 105° C. for 10 minutes. After drying the swatches were tested using the conventional TEGEWA method (Method and standard scales obtainable from Verband TEGEWA, Karlstrasse 21, Frankfurt a.M., Germany).

TEGEWA method

The samples of desized fabric were impregnated in a saturated iodine solution (5 ml/100 ml water), rinsed with cold water, and wiped off with filter paper before comparing the (blue) colour intensity with the TEGEWA violet standard scale.

The TEGEWA standard scale ranges from 1 to 9, where 1 is the sized fabric while 9 is the totally desized fabric. A rating above 6 usually corresponds to an acceptable desizing.

The results from the pH experiments are shown in table 1 below.

TABLE 1

| pH | Reference | Enzyme B (conventional) | Enzyme A (ox. stable) |
|---|---|---|---|
| 7 | 1 | 6 | 7 |
| 8 | 1 | 5 | 7 |
| 9 | 1 | 4 | 7 |
| 10 | 1 | 2 | 5 |

The results show that the oxidation stable A-amylase is more pH-stable than the conventional A-amylase (Termamyl).

EXAMPLE 2

The oxidation stable α-amylase was tested and compared with a conventional amylase (Termamyl) in a combined process of desizing/bleaching.
Materials and methods
  As described in example 1, and further:
  $H_2O_2$ concentration: 4, 6, 8, 10, 24 g/l, respectively
  NaOH conc.: 0.5, 1.0 g/l, respectively
  Stabilizer: 2 g/l (Product No. 1136 from the company Harald Pedersen, Kastanievej 7, 1878 Frb.C, Denmark)
  Process temp.: 80° C., 85° C., 95° C., respectively
  Process time: 60 minutes (20 min. for temp. 85° C. and 95° C.)

The desizing/bleaching solution was preheated to 80° C. (85° C., 95° C.) in a shake flask, the swatches were added to the solution, and the shake flask was placed in a shaking water bath for 1 hour. The concentration of $H_2O_2$ in the solution was monitored by titration immediately before use. The washing/rinsing and evaluation of the treated swatches was as described in example 1.

The results from the desizing/bleaching experiments are shown in table 2 below.

TABLE 2

| $H_2O_2$ g/l | Temp. °C. | NaOH g/l | pH | Reference score | Enzyme B score | Enzyme A score |
|---|---|---|---|---|---|---|
| 4 | 80 | 0.5 | 10.1 | 2 | 5 | 7 |
| 6 | 80 | 0.5 | 9.9 | 1 | 3 | 6 |
| 6 | 80 | 1.0 | 10.1 | 2 | 3 | 5 |
| 8 | 80 | 1.0 | 10.2 | 2 | 3 | 5 |
| 10 | 85 | 0.5 | 9.6 | 2 | 4 | 5 |
| 10 | 95 | 0.5 | 9.5 | 3 | 5 | 6 |
| 24 | 85 | 0.5 | 9.1 | 3 | 4 | 6 |
| 24 | 95 | 0.5 | 8.7 | 4 | 5 | 7 |
| 10 | 95 | 1.0 | 10.0 | 3 | 4 | 5 |

The results demonstrate that the oxidation stable A-amylase is more stable at high pH and at high $H_2O_2$ concentrations than the conventional amylase (Termamyl).

References Cited in the Specification

Gray, G. L. et al., J. Bacteriol. 166, 635–643, 1986;
Takkinen et al., J. Biol. Chem. 258, 1007–1013, 1983;
Lipman and Pearson, Science 227, 1435 (1985);
Hudson, L., and Hay, F., Practical Immunology, Third edition (1989), Blackwell Scientific Publications;
Sambrook et al., *Molecular Cloning: A Laboratory Manual*, 2nd Ed., Cold Spring Harbor, 1989;
Nakajima, R. et al., 1986, Appl. Microbiol. Biotechnol. 23, 355–360;
Liisa Holm et al., 1990, Protein Engineering 3, 181–191;
Greer, J., 1981, J. Mol. Biol. 153, 1027–1042;
Olson, E. S. "Textile Wet Processes, Vol. I, Noyes Publication, Park Ridge, N.J., USA (1983);
M. Peter und H. K. Rouette, Grundlagen der Textilveredlung, Deutsche Fachverlag GmbH, Frankfurt am Main, Germany (1988);

---

We claim:

1. A process for simultaneously desizing and bleaching a sized fabric containing starch or starch derivatives, said process comprising treating the fabric with a bleaching composition and an oxidation stable α-amylase, wherein the α-amylase comprises the amino acid sequence of SEQ ID NO:2 or an analogue of said α-amylase, which i) is at least 60% homologous with the sequence shown in SEQ ID NO:2, ii) reacts with an antibody raised against said α-amylase, and iii) is encoded by a DNA sequence which hybridizes with the same probe as a DNA sequence encoding the α-amylase having the amino acid sequence of SEQ ID NO:2.

2. The process of claim 1, wherein the α-amylase is derived from *Bacillus licheniformis*, *Bacillus amyloliquefaciens* or *Bacillus stearothermophilus*.

3. The process of claim 1, wherein the methionine residue in position 197 of the α-amylase of SEQ ID NO:2 has been replaced with an amino acid selected from the group consisting of Leu, Thr, Ala, Gly, Ser, Ile and Asp.

4. A process for simultaneously desizing and bleaching a sized fabric containing starch or starch derivatives, said process comprising treating the fabric with a bleaching composition and an oxidation stable α-amylase, wherein the α-amylase comprises the amino acid sequence of SEQ ID NO:4 or an analogue of said α-amylase, which i) is at least 60% homologous with the sequence shown in SEQ ID NO:4, ii) reacts with an antibody raised against said α-amylase, and iii) is encoded by a DNA sequence which hybridizes with the same probe as a DNA sequence encoding the α-amylase having the amino acid sequence of SEQ ID NO:4.

5. The process of claim 4, wherein the α-amylase is derived from *Bacillus licheniformis, Bacillus amyloliquefaciens* or *Bacillus stearothemophilus*.

6. The process of claim 5, wherein the α-amylase is derived from *Bacillus licheniformis, Bacillus amyloliquefaciens* or *Bacillus stearothermophilus*.

7. A process for simultaneously desizing and bleaching a sized fabric containing starch or starch derivatives, said process comprising treating the fabric with a bleaching composition and an oxidation stable α-amylase, wherein the α-amylase comprises the amino acid sequence of SEQ ID NO:6 or an analogue of said α-amylase, which i) is at least 60% homologous with the sequence shown in SEQ ID NO:6, ii) reacts with an antibody raised against said α-amylase, and iii) is encoded by a DNA sequence which hybridizes with the same probe as a DNA sequence encoding the α-amylase having the amino acid sequence of SEQ ID NO:6.

8. The process of claim 7, wherein the methionine residue in position 200 and/or 206 of the α-amylase of SEQ ID NO:6 has been replaced with an amino acid selected from the group consisting of Leu, Thr, Ala, Gly, Ser, Ile and Asp.

9. A process for simultaneously desizing and bleaching of a sized fabric containing starch or starch derivatives, which process comprises treating the fabric with a bleaching composition and an oxidation stable α-amylase, wherein the oxidation stable α-amylase has been prepared from a parent α-amylase by replacing one or more methionine residues of the parent α-amylase with an amino acid selected from the group consisting of Leu, Thr, Ala, Gly, Ser, Ile and Asp.

10. The process of claim 9, further comprising adding a stabilizer and/or a wetting agent.

11. The process of claim 9, wherein the bleaching composition is hydrogen peroxide.

12. The process of claim 11, wherein the oxidation stable α-amylase is used in an amount of 1–10 g/l and/or the hydrogen peroxide is used in an amount of 1–50 g/l.

13. The process of claim 9, wherein the combined desizing and bleaching process is performed at a temperature in the range of 30–100° C. and a pH in the range of 6.5–11.

14. The process of claim 9, wherein the oxidation stable α-amylase is used in an amount of 1–5 g/l.

15. The process of claim 14, wherein the oxidation stable α-amylase is used in an amount of 1–3 g/l.

16. A composition for use in a simultaneous desizing and bleaching process comprising an oxidation stable α-amylase in combination with at least one further component selected from the group consisting of wetting agents, dispersing agents, sequestering agents and emulsifying agents, wherein the oxidation stable α-amylase has been prepared from a parent α-amylase by replacing one or more methionine residues of the parent α-amylase with an amino acid selected from the group consisting of Leu, Thr, Ala, Gly, Ser, Ile and Asp.

* * * * *